United States Patent [19]
Ye et al.

[11] Patent Number: 5,997,899
[45] Date of Patent: Dec. 7, 1999

[54] METHOD FOR PRODUCING LIPOSOMES WITH INCREASED PERCENT OF COMPOUND ENCAPSULATED

[75] Inventors: Qiang Ye; Mantripragada Bhima Sankaram, both of San Diego, Calif.

[73] Assignee: SkyePharma Inc., San Diego, Calif.

[21] Appl. No.: 08/723,583

[22] Filed: Oct. 1, 1996

[51] Int. Cl.$^6$ ..................................................... A61K 9/127
[52] U.S. Cl. ............................................................. 424/450
[58] Field of Search ................................... 424/450, 1.21, 424/9.321, 9.51, 417; 264/4.1, 4.3, 4.6; 436/829; 935/54

[56] References Cited

U.S. PATENT DOCUMENTS

| | | |
|---|---|---|
| 4,078,052 | 3/1978 | Papahadjopoulos . |
| 4,089,801 | 5/1978 | Schneider . |
| 4,145,410 | 3/1979 | Sears . |
| 4,224,179 | 9/1980 | Schneider . |
| 4,235,871 | 11/1980 | Papahadjopoulos et al. . |
| 4,310,506 | 1/1982 | Baldeschwieler et al. . |
| 4,394,372 | 7/1983 | Taylor . |
| 4,522,803 | 6/1985 | Lenk et al. . |
| 4,588,578 | 5/1986 | Fountain et al. . |
| 4,599,227 | 7/1986 | Dees et al. . |
| 4,610,868 | 9/1986 | Fountain et al. . |
| 4,752,425 | 6/1988 | Martin et al. . |
| 4,769,250 | 9/1988 | Forssen . |
| 4,781,871 | 11/1988 | West, III et al. . |
| 4,920,016 | 4/1990 | Allen et al. . |
| 5,000,959 | 3/1991 | Iga et al. . |
| 5,021,200 | 6/1991 | Vanlerberghe et al. . |
| 5,077,056 | 12/1991 | Bally et al. . |
| 5,204,112 | 4/1993 | Hope et al. . |
| 5,211,955 | 5/1993 | Legros et al. . |

FOREIGN PATENT DOCUMENTS

| | | |
|---|---|---|
| 2050287 | 1/1981 | United Kingdom . |

OTHER PUBLICATIONS

Chapman in Liposome technology vol. 1. pp. 1–19. CRC Press, Ed. by Gregoriadis G., 1984.

Studies on Phosphatidylcholine Vesicles Formation and Physical Characteristics Huang, *Biochemistry*, 8:334–352, 1969.

Diffusion of Univalent Ions Across The Lamellae of Swollen Phospholipids Bangham, *J. Mol. Bio.*, 13:238–252, 1965.

Comparative Properties and Methods of Preparation of Lipid Vesicles (Liposomes) Szoka, et al., *Ann. Rev. Biophys. Bioengineering*, 9:467–508, 1980.

Evaluation of Retinal Toxicity and Liposome Encapsulation of the Anti–CMV Drug 2'–nor–cyclic GMP Shakiba, et al., *Investigative Ophthalmology and Visual Science*, No. 10 34:2903–2910, Sep. 1993.

Fibrin–Enmeshed Tobramycin Liposomes: Single Application Topical Therapy of . . . Frucht–Perry, et al., *Cornea*, No. 5, 11:393–397, Sep. 1992.

Tobramycin Liposomes. Single Subconjunctival Therapy of . . . Assil, et al., *Investigative Ophthalmology and Visual Science*, No. 13, 32:3216–3220, Dec. 1991.

Liposome Suppression of Proliferative Vitreoretinopathy. Rabbit . . . Assil, et al., *Investigative Ophtahlmology and Visual Science*, No. 11, 32:2891–2897, Oct. 1991.

Magnetic Resonance Imaging of Rabbit Brain After Intracarotid Injection . . . Turski, et al., *Magnetic Resonance in Medicine*, No. 2, 7:184–196, Jun. 1988.

Filtering Surgery in Owl Monkeys Treated With the Antimetabolite . . . Skuta, et al., *American Journal of Ophthalmology*, No. 5, 103:714–716, May 15, 1987.

(List continued on next page.)

*Primary Examiner*—Gollamudi S. Kishore
*Attorney, Agent, or Firm*—Fish & Richardson P.C.

[57] ABSTRACT

The efficiency of encapsulating a drug into a liposomal formulation is increased by use of a lipid having a carbon chain containing from about 13 to about 28 carbons during preparation of the liposomes. Preferably the liposomes are multivesicular liposomes.

20 Claims, 2 Drawing Sheets

OTHER PUBLICATIONS

Multivesicular Liposomes. Sustained Release of the Antimetabolite . . . Assil, et al., *Archives of Ophthalmology*, No. 3, 105:400–403, Mar. 1987.

Weak Acid–Induced Release of Liposome–Encapsulated Carboxyfluorescein Barbet, et al., *Biochimica et Biophysica Acta*, No. 3, 772:347–356, May 30, 1984.

Preparation of Cell–Size Unilamellar Liposomes with High Captured Volume and Defined Size . . . Kim, et al., *Biochim. Biophys. Acta*, 646:1–9, 1981.

Preparation of Multivesicular Liposomes Kim, et al., *Biochim. Biophys. Acta*, 728:339–348, 1983.

Preparation of Multilamellar Vesicles of Defined Size–Distribution by Solvent–Spherule . . . Kim, et al., *Biochim. Biophys. Acta*, 812:793–801, 1985.

Multivesicular Liposomes Containing Cytarabine Entrapped in the Presence of . . . Kim, et al., *Cancer Treat. Rep.*, 71:705–711, 1987.

Multivesicular Liposomes Containing Cytosine 1–$\mu$–D–Arabinofuranosylcytosine for Slow–Release Intrathecal Therapy Kim, et al., *Cancer Research*, 47:3935–3937, 1987.

Multivesicular Liposomes Containing Cytosine for Slow Release . . . Kim, et al., *Cancer Treat Rep.*, 71:447–450, 1987.

Modulation of the Peritoneal Clearance of Liposomal Cytosine Arabinoside by . . . Kim, et al., *Cancer Chemother. Pharmacology*, 19:307–310, 1987.

Multivesicular Liposomes Containing Bleomycin for Subcutaneous Administration Roy, et al., *Cancer Chemother. Pharmacology*, 28:105–108, 1991.

Prolongation of Drug Exposure in Cerebrospinal Fluid by Encapsulation Into . . . Kim, et al., *Cancer Research*, 55:1596–1598, Apr. 1, 1993.

Direct Cerebrospinal Fluid Delivery of an Antiretroviral Agent Using . . . Kim, et al., *Jrnl. of Infectious Diseases.*, 162:750–752, 1990.

Treatment of Leptomeningeal Metastasis with Intraventricular Administration of . . . Chamberlain, et al., *Archives of Neurol*, No. 3, 50:261–264, 1993.

A Slow–Release Methotrexate Formulation for Inrathecal Chemotherapy Chatelut, et al., *Cancer Chemother. Pharmacol.*, 32:179–182, 1993.

Quantitative Cerebrospinal Fluid Cytology in Patients Receiving Intracavitary Chemotherapy Russack, et al., *Ann. Neurol.*, 34:108–112, 1993.

Extended Cerebrospinal–Fluid Cytarabine Exposure Following Intrathecal Administration of DTC 101 Kim, et al., *J. Clin. Oncol.*, 11:2186–2193, 1993.

Liposomes as Carriers of Cancer Chemotherapy: A Review Kim, *Drugs*, No. 4, 46:618–638, 1993.

Extended–Release Formulation of Morphine for Subcutaneous Administration Kim, et al., *Cancer Chemother. Pharmacol.*, 33:187–190, 1993.

Production and Size Control of Large Unilamellar Liposomes by Emulsification Ishii, *Liposome Technology*, 1:111–121, 1993.

Structural Properties and Functional Roles of Phospholipids In . . . Cullis, et al., *Phospholipids and Cellular Regulation*, 1:65–123, 1985.

An Extended–Release Formulation of Methotrexate For Subcutaneous . . . Bonetti, et al., *Cancer Chemotherapy and Pharmacology.*, In Press, 1994.

Novel Multilayered Lipid Vesicles: Comparison of Physical Characteristics of Multilamellar Liposomes and Stable Plurilamellar Vesicles Grunor, et al., *Biochemistry*, No. 12, 24:2833–2842, Jun. 4, 1985.

METHOD FOR PRODUCING LIPOSOMES WITH INCREASED PERCENT OF COMPOUND ENCAPSULATED

BACKGROUND OF THE INVENTION

This invention relates to liposomal formulations of compounds such as drugs. More particularly this invention relates to methods of increasing the encapsulation of desired compounds in liposomal formulations and the methods of making them.

When phospholipids and many other amphipathic lipids are dispersed gently in an aqueous medium they swell, hydrate and spontaneously form multilamellar concentric bilayer vesicles with layers of aqueous media separating the lipid bilayers. These systems commonly are referred to as multilamellar liposomes or multilamellar vesicles (MLV) and usually have diameters of from 0.2 $\mu$m to 5 $\mu$m. Sonication of MLV results in the formation of small unilamellar vesicles (SUV) with diameters usually in the range of 20 to 100 nm, containing an aqueous solution in the core. Multivesicular liposomes (MVL) differ from multilamellar liposomes in the random, non-concentric arrangement of chambers within the liposome. Amphipathic lipids can form a variety of structures other than liposomes when dispersed in water, depending on the molar ratio of lipid to water, but at low ratios the liposome is the preferred structure.

The physical characteristics of liposomes generally depend on pH and ionic strength. They characteristically show low permeability to ionic and polar substances, but at certain temperatures can undergo a gel-liquid crystalline phase (or main phase) transition dependent upon the physical properties of the lipids used in their manufacture which markedly alters their permeability. The phase transition involves a change from a closely packed, ordered structure, known as the gel state, to a loosely packed, less-ordered structure, known as the liquid crystalline state.

Various types of lipids differing in chain length, saturation, and head group have been used in liposomal drug formulations for years, including the unilamellar, multilamellar, and multivesicular liposomes mentioned above. One of the major goals of the field is to develop liposomal formulations for sustained release of drugs and other compounds of interest, and liposomal formulations from which the rate of release of the encapsulated compound can be controlled.

These goals are important and many studies have been undertaken towards achieving them. Another less recognized goal, increasing the yield of product from a liposomal formulation used as a delivery agent, has very practical benefits as well, particularly to the pharmaceutical industry. For instance, increasing the percent of drug encapsulated in liposomal formulations can result in increased yield and substantial cost savings. In the case of liposomal drug formulations, it is also desirable to have the highest possible percent of drug encapsulated for any given lipid:drug ratio to avoid the need for injecting highly viscous formulations or large volumes into the patient in order to achieve a desired dosage. If a process results in a high percentage of compound encapsulated but yields a product with a low drug:lipid ratio, it is generally necessary that the formulation have a high lipocrit (analogous to hematocrit) in order to satisfy a specified drug dose, or provide a therapeutically effective amount of a biologically active substance via an injection. Analogous to hematocrit, lipocrit is a measure of the percent volume occupied by the liposomes relative to the total volume of the liposome suspension. Yet, such formulations are difficult to administer by injection because of their high viscosities. Thus, the need exists for more and better methods for obtaining liposomal formulations that maximize the efficiency of a drug encapsulation to achieve a low lipid:drug ratio.

SUMMARY OF THE INVENTION

A method is provided for increasing the percent of a compound, such as a drug, that is encapsulated in a liposomal formulation comprising increasing the number of carbons in the carbon chain of at least one lipid in the lipid component of the liposome, wherein the chemical structures of the two lipids are otherwise substantially similar. The preferred length of carbon chain in at least one lipid in a multivesicular liposome is increased to an integer in the range from about 13 to about 28, most preferably about 13 to 22. The preferred lipids of increased carbon chain length are phospholipids.

DETAILED DESCRIPTION OF THE PREFERRED EMBODIMENTS

Figure 1:
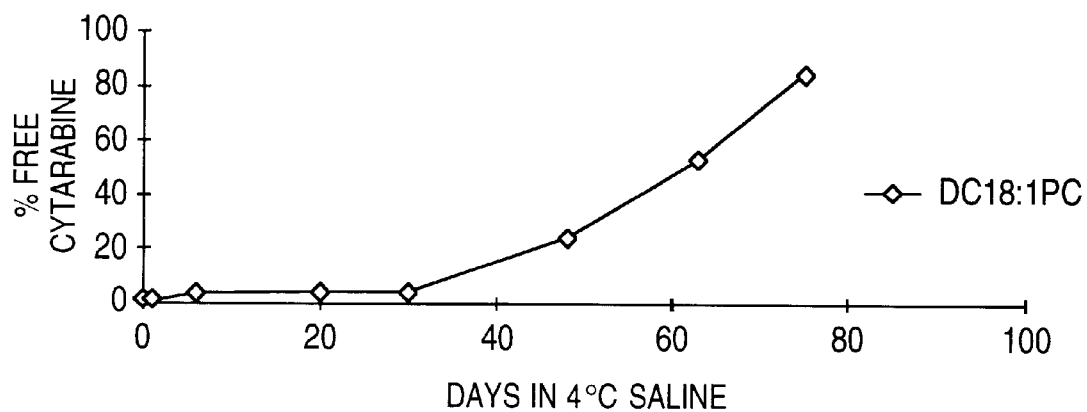
FIG. 1 is a graph illustrating the drug release profile at 4° C. of multivesicular liposomes made with DC18:1PC. The encapsulated drug is cytarabine.

The present invention provides a method for increasing the efficiency with which a compound is encapsulated into a liposomal formulation. It has surprisingly been discovered that, in liposomal formulations, the encapsulation efficiency of the active substance can be significantly increased by increasing the number of carbons in the carbon chain of at least one of the amphipathic lipids used in preparation of the liposomal formulation. This invention is particularly useful in the pharmaceutical industry for increasing the efficiency with which a pharmacologically active amount of a biologically active compound is encapsulated in a liposome without substantially increasing the lipocrit of the formulation for a given drug dose. The method of the invention is useful for increasing the encapsulation efficiency of any type of liposome, but in a preferred embodiment a method for increasing encapsulation efficiency during manufacture of a multivesicular liposomal formulation is provided.

There are at least three types of liposomes. The term "multivesicular liposomes (MVL)" as used throughout the specification and claims means man-made, microscopic lipid vesicles comprising lipid membranes enclosing multiple non-concentric aqueous chambers. In contrast, "multilamellar liposomes or vesicles(MLV)" have multiple "onion-skin" concentric membranes, in between which are shell-like concentric aqueous compartments. Multilamellar liposomes and multivesicular liposomes characteristically have mean diameters in the micrometer range, usually from 0.5 to 25 $\mu$m. The term "unilamellar liposomes or vesicles (ULV)" as used herein refers to liposomal structures having a single aqueous chamber, usually with a mean diameter range from about 20 to 500 nm.

Multilamellar and unilamellar liposomes can be made by several relatively simple methods. The prior art describes a number of techniques for producing ULV and MLV (for example U.S. Pat. Nos. 4,522,803 to Lenk; 4,310,506 to Baldeschweiler; 4,235,871 to Papahadjopoulos; 4,224,179 to Schneider, 4,078,052 to Papahadjopoulos; 4,394,372 to Taylor 4,308,166 to Marchetti; 4,485,054 to Mezei; and 4,508,703 to Redziniak).

By contrast, production of multivesicular liposomes requires several process steps. Briefly, the preferred method for making MVL is as follows: The first step is making a "water-in-oil" emulsion by dissolving at least one amphipathic lipid and at least one neutral lipid in one or more volatile organic solvents for the lipid component, adding to the lipid component an immiscible first aqueous component and a biologically active substance to be encapsulated, and optionally adding, to either or both the lipid component and the first aqueous component, an acid or other excipient for modulating the release rate of the encapsulated biologically active substances from the MVL. The mixture is emulsified, and then mixed with a second-immiscible aqueous component to form a second emulsion. The second emulsion is mixed either mechanically, by ultrasonic energy, nozzle atomization, and the like, or by combinations thereof, to form solvent spherules suspended in the second aqueous component. The solvent spherules contain multiple aqueous droplets with the substance to be encapsulated dissolved in them (see Kim et al., *Biochem. Biophys. Acta*, 728:339–348, 1983). For a comprehensive review of various methods of ULV and MLV preparation, refer to Szoka, et al. *Ann. Rev. Biophys. Bioeng.* 9:465–508, 1980.

The term "solvent spherule" as used throughout the specification and claims means a microscopic spheroid droplet of organic solvent, within which are multiple smaller droplets of aqueous solution. The solvent spherules are suspended and totally immersed in a second aqueous solution.

The term "neutral lipid" means an oil or fat that has no membrane-forming capability by itself and lacks a hydrophilic "head" group.

The term "amphipathic lipid" means a molecule that has a hydrophilic "head" group and hydrophobic "tail" group and has membrane-forming capability.

The term "zwitterionic lipid" means an amphipathic lipid with a net charge of zero at pH 7.4.

The term "anionic lipid" means an amphipathic lipid with a net negative charge at pH 7.4.

The term "cationic lipid" means an amphipathic lipid with a net positive charge at pH 7.4.

For making multivesicular liposomes, it is required that at least one amphipathic lipid and one neutral lipid be included in the lipid component. The amphipatnic lipids can be zwitterionic, anionic, or cationic lipids. Examples of zwitterionic amphipathic lipids are phosphatidylcholines, phosphatidylethanolamines, sphingomyelins etc. Examples of anionic amphipathic lipids are phosphatidylglycerols, phosphatidylserines, phosphatidylinositols, phosphatidic acids, etc. Examples of cationic amphipathic lipids are diacyl trimethylammoniumpropane and ethyl phosphatidylcholine. Examples of neutral lipids include diglycerides, such as diolein, dipalmitolein, and mixed caprylin-caprin diglycerides; triglycerides, such as triolein, tripalmitolein, trilinolein, tricaprylin, and trilaurin; vegetable oils, such as soybean oil; animal fats, such as lard and beef fat; squalene; tocopherol; and combinations thereof. Additionally, cholesterol or plant sterols can be used in making multivesicular liposomes.

As used herein, "percent encapsulation of drug, or other compound" means the ratio of the amount of compound to be encapsulated in the final suspension of the liposome manufacturing process to the total amount of compound to be encapsulated used in the first aqueous solution of the process multiplied by 100.

$$\begin{array}{c}\text{Percent encapsualtion}\\\text{of compound}\end{array} = \left[\frac{\text{Amt. of compound encapsulated}}{\begin{array}{c}\text{Amt. of compound introduced}\\\text{prior to encapsulation}\end{array}}\right] \times 100$$

As used herein, "lipocrit," which is defined in analogy to hematocrit, means the ratio of the volume occupied by the liposomes to the total suspension volume multiplied by 100.

$$\begin{array}{c}\text{Lipocrit}\\\text{(in percent)}\end{array} = \left[\frac{\text{Volume occupied by the liposomes}}{\text{Total volume of liposome suspension}}\right] \times 100$$

As used herein, "percent free drug" means the ratio of the amount of drug exterior to the liposomes in the final liposome suspension to the total amount of drug in the final suspension (the final product) multiplied by 100.

$$\begin{array}{c}\text{Percent}\\\text{free drug}\end{array} = \left[\frac{\begin{array}{c}\text{Amt. of drug exterior to the liposomes}\\\text{in the final product}\end{array}}{\text{Amt. of drug in final product}}\right] \times 100$$

The methods for determining these parameters are illustrated in Example 2 of this application.

As used herein the term "therapeutically effective amount" means the amount of a biologically active substance necessary to induce a desired pharmacological effect. The amount can vary greatly according to the effectiveness of a particular active substance, the age, weight, and response of the individual host as well as the nature and severity of the host's symptoms. Accordingly, there is no upper or lower critical limitation upon the amount of the active substance. The therapeutically effective amount to be employed in the present invention can readily be determined by those skilled in the art.

In the method of the present invention, the encapsulation efficiency of any given liposomal formulation employing short chain amphipathic lipids, having 12 or less carbons in the carbon chain, can be increased by increasing the chain length within any given lipid used in the formulation of the liposome, generally from a carbon chain length of 13 to about 28 carbons, and preferably from about 18 to about 22 carbons. This general rule holds whether the carbon chain of the amphipathic lipid to be changed is saturated, or whether it contains one or more double bonds. Generally, however, in selecting the lipids to be used in formulating a multivesicular liposome it should be kept in mind that it is possible to use an organic solvent with a lower boiling point when utilizing a lipid with a given number of carbons in the carbon chain, if the lipid contains at least one double bond in the carbon chain. The preferred amphipathic lipids for use in making the multivesicular liposomes with increased encapsulation efficiency are phospholipids because phospholipids are natural lipids found in the body.

A representative list of long chain amphipathic lipids preferred for use in the practice of this invention follows. This list is illustrative and not intended to in any way limit the scope of the invention. Also included are the abbreviations used to refer to the phospholipids in this application.

DOPC or DC18:1PC=1,2-dioleoyl-sn-glycero-3-phosphocholine
DLPC or DC12:0PC=1,2-dilauroyl-sn-glycero-3-phosphocholine
DMPC or DC14:0PC=1,2-dimyristoyl-sn-glycero-3-phosphocholine
DPPC or DC16:0PC=1,2-dipalmitoyl-sn-glycero-3-phosphocholine
DSPC or DC18:0PC=1,2-distearoyl-sn-glycero-3-phosphocholine
DAPC or DC20:0PC=1,2-diarachidoyl-sn-glycero-3-phosphocholine
DBPC or DC22:0PC=1,2-dibehenoyl-sn-glycero-3-phosphocholine
DC16:1PC=1,2-dipalmitoleoyl-sn-glycero-3-phosphocholine
DC20:1PC=1,2-dieicosenoyl-sn-glycero-3-phosphocholine
DC22:1PC=1,2-dierucoyl-sn-glycero-3-phosphocholine
DPPG=1,2-dipalmitoyl-sn-glycero-3-phosphoglycerol
DOPG =1,2-dioleoyl-sn-glycero-3-phosphoglycerol The term "biologically active compound" as used herein means a chemical compound that is known in the art as having utility for modulating biological processes so as to achieve a desired effect in modulation or treatment of an undesired existing condition in a living being, such as a medical, agricultural or cosmetic effect. Thus, biologically active substances are generally selected from the broad categories of medicaments, pharmaceuticals, radioisotopes, agricultural products and cosmetics.

Therapeutic biologically active compounds, or drugs for encapsulation in the methods and compositions of this invention may be selected from the general group consisting of anti-neoplastic agents, anti-infective agents, hormones, anti-depressives, antiviral agents, anti-nociceptive agents, anxiolytics and biologics.

Representative examples of anti-neoplastic agents useful in the compositions and methods of the present invention include methotrexate, taxol, tumor necrosis factor, chlorambucil, interleukins, etoposide, cytarabine, fluorouracil and vinblastine.

Representative examples of anti-infective agents useful in the compositions and methods of the present invention include pentamidine, metronidazole, penicillin, cephalexin, tetracyclin and chloramphenicol.

Representative examples of anti-viral agents useful in the composition and methods of the present invention include dideoxycytidine, zidovudine, acyclovir, interferons, dideoxyinosine and ganciclovir.

Representative examples of anxiolytics and sedatives useful in the compositions and methods of the invention include benzodiazepines such as diazepam, barbiturates such as phenobarbital and other compounds such as buspirone and haloperidol.

Representative examples of hormones useful in the compositions and methods of the present invention include estradiol, prednisone, insulin, growth hormone, erythropoietin, and prostaglandins.

Representative examples of anti-depressives useful in the compositions and methods of the present invention include fluoxetine, trazodone, imipramine, and doxepin.

Representative examples of anti-nociceptives useful in the compositions and methods of the present invention include hydromorphine, oxycodone, fentanyl, morphine and meperidine.

The term "biologics" encompasses nucleic acids (DNA and RNA), proteins and peptides, and includes compounds such as cytokines, hormones (pituitary and hypophyseal hormones), growth factors, vaccines etc. Of particular interest are interleukin-2, insulin-like growth factor-1, interferons, insulin, heparin, leuprolide, granulocyte colony stimulating factor (GCSF), granulocyte-macrophage colony stimulating factor (GM-CSF), tumor necrosis factor, inhibin, tumor growth factor alpha and beta, Mullerian inhibitory substance, calcitonin, and hepatitis B vaccine.

The biologically active substance can be employed in the present invention in various forms, such as molecular complexes or biologically acceptable salts. Representative examples of such salts are succinate, hydrochloride, hydrobromide, sulfate, phosphate, nitrate, borate, acetate, maleate, tartrate, salicylate, metal salts (e.g., alkali or alkaline earth), ammonium or amine salts (e.g., quarternary ammonium) and the like. Furthermore, derivatives of the active substances such as esters, amides, and ethers which have desirable retention and release characteristics but which are readily hydrolyzed by physiological pH or enzymes in vivo can also be involved.

The method of this invention is practiced by substituting a short chain lipid of a particular type, such as a phospholipid, generally one having less than 12 carbons in the hydrocarbon chain, with one having 1 or more additional carbons in the chain, generally with one having 13 to about 22 carbons. For instance, the encapsulation efficiency of a liposomal formulation can be increased by substituting a 13 carbon lipid for a 12 carbon lipid, or by substituting a 16 carbon lipid for a 14 carbon lipid, wherein the chemical structure of the two lipids is otherwise substantially similar, and the composition of the liposomal formulation is otherwise unchanged. As shown in Table 2, the encapsulation efficiency of cytarabine increased monotonically from 0.2% up to 56.9% when a 12 carbon saturated PC was replaced by a longer chain saturated PC of 14 to 18 carbons. As is also shown in Table 2, the encapsulation efficiency of cytarabine increased from 30.1% to 44.6% when a 16 carbon unsaturated PC was replaced by an 18 carbon unsaturated PC having the same number of double bonds at the same position (position 9) in the acyl chain, and increased from 44.6% to 57.5% when an 18 carbon unsaturated PC was replaced by a 20 carbon unsaturated PC having the same number of double bonds, but located at a different position (position 11) in the acyl chain. However, an increase in the percent compound encapsulated will not necessarily result from substituting a 13 carbon unsaturated lipid for a 12 carbon saturated lipid, or a 13 carbon phospholipid for a 12 carbon phospholipid, if the chemical structures of the two lipids differ substantially in other respects, i.e., if the lipid head groups, the stereochemistry (such as changing a cis to a trans, or a D-type to an L-type, or exhanging other types of stereoisomers), or the number of double bonds within the two unsaturated lipids is different.

Preferably, the method of increasing the encapsulation efficiency of a liposomal formulation is applied to techniques for encapsulating biologically active substances into MVL. Generally, the encapsulation efficiency of a liposomal formulation can be increased by at least 30%, and in MVL the percent encapsulation of the active substance is increased to as great as 65%, or even to as great as 85%, depending upon the chemical characteristics of the lipids and biologically active substances used in the formulation. For example, it has been discovered that the efficiency of encapsulating leuprolide into a multivesicular liposomal formulation can be increased five fold by increasing the number of carbons from 12 to 20 in a saturated phospholipid used in formation of the liposome, while the particle diameter is increased only from 10.9 $\mu$m to 15.1 $\mu$m. The diameter of liposomes of the invention is generally less than 50 μm and preferably less than 25 μm. The resulting change in the lipocrit of the formulations is only from 35.8 to 40.1% for a similar drug concentration in the liposome suspension. In addition, for a given drug concentration in the final liposome suspension, an MLV formulation would have a significantly higher lipocrit than a MVL formulation. For instance, an MLV formulation of cytarabine using DSPC has a lipocrit of 24.6 for a drug concentration of 3.5 mg/mL; whereas an MVL formulation using DSPC has a lipocrit of 26.8, and a drug concentration of 10.2 mg/mL, which is three times higher.

This finding is not particular to multivesicular liposomes. An increase in the encapsulation efficiency of multilamellar liposomes is also seen with increase in the number of carbons in the chain of at least one of the lipids used in manufacture, as is illustrated in Example 8 below. However, in multilamellar liposomes the increase is not generally as great as in multivesicular lipcsomes, and is generally in the range from 6 to 50%. For instance, as shown in Example 8, in a multilamellar formulation an increase in the number of carbons in the phospholipid carbon chain from 14 to 18 resulted in an increase in encapsulation efficiency from 6.5 to 44.2%.

An increase in encapsulation efficiency with increasing number of carbons in the phospholipid used in making the liposome is also obtained when an unsaturated phospholipid is introduced into the formulation. Generally, in MVL, increasing the number of carbons in the chain of the unsaturated phospholipid results in an increase of encapsulation efficiency in the range of from 30% to 80% with relatively small corresponding increase in particle diameter. For instance, when leuprolide is encapsulated into multivesicular liposomes comprising an unsaturated phospholipid with one double bond, and the number of carbons in the phospholipid carbon chain is increased from 18 to 22, the encapsulation efficiency increases from 55.4% to 83.3%, while the mean particle diameter increases from 9.7 to 14.3 μm.

In principle, there is no upper limit on the length of the lipid carbon chain that can be used to increase the encapsulation efficiency, except that imposed by the phase transition temperature of the lipids at process conditions. In formulating MVL used in the method of this invention there are three temperatures to take into consideration: the boiling point of the solvent; the gel-liquid crysalline phase transition temperature of the lipid; and the process temperature. Of these, the boiling point of the solvent should be the highest, and the phase transition temperature of the lipid(s) should be the coolest, with the process temperature in between. Thus the chain length of the lipid should be selected to have a gel-liquid crystalline phase transition temperature less than 100° C. at STP for an aqueous solvent. Additionally, for best encapsulation efficiency, when saturated lipids are used in the formulation of multivesicular liposomes, it is usually required that the emulsification be performed at a temperature above the gel-liquid crystalline transition temperature of the lipid used in manufacture of the solvent spherules.

As used herein, the "shelf life" of a liposomal formulation is related to the rate of release of the encapsulated substance from a liposomal formulation in a storage solution, for instance normal saline (0.9% sodium chloride), at a storage temperature, for instance at 4° C. The shelf life of multivesicular liposomal formulations whose encapsulation efficiency is increased by incorporation of a long chain amphipathic lipid, for instance one containing from 13 to 28 carbons, as taught herein, is also significantly increased in proportion to the increase in the number of carbons in the carbon chain.

In one embodiment, therefore, the present invention provides a liposomal composition comprising a pharmacologically active amount of a biologically active compound encapsulated in a multivesicular liposome formulation wherein the formulation comprises at least one amphipathic lipid having a carbon chain containing 13 to 28, and preferably from 13 to 22 carbons. Such multivesicular liposomes can be made by the process described herein and inherently possess the capacity to encapsulate the biologically active compound with a greater efficiency than any other known type of liposome and with an efficiency that increases in direct proportion with the number of carbons in the carbon chain of the amphipathic lipid(s) used in preparation of the formulation. Preferably, at least one of the long chain amphipathic lipids in the multivesicular liposomes is a phospholipid, and is most preferably a phosphocholine.

The compositions and methods of the invention present several advantages, especially to the pharmaceutical industry. Thus, improved encapsulation efficiency results in improved yields and cost savings.

The methods of achieving a high encapsulation of compound of this invention generally allow for production of liposomal formulations characterized by a higher drug:lipid ratio for any given drug than can be achieved by other methods of encapsulation. A high drug-lipid ratio is of practical importance to liposomal systems for in vivo administration of drugs and other therapeutic compounds because liposomal formulations made for injection into a body must generally have a lipocrit less than about 60% to be considered injectable, yet preferably contain a therapeutically effective amount of the encapsulated drug in a single dose to avoid repeated injections. Therefore, formulations that combine a high drug encapsulation efficiency and a high drug:lipid ratio are especially preferred for therapeutic treatments in which drugs are encapsulated in liposomal formulations for administration to patients by injection and can be achieved using the methods of this invention.

The following examples illustrate the manner in which the invention can be practiced. It is understood, however, that the examples are for the purpose of illustration, and the invention is not to be regarded as limited to any of the specific materials or conditions therein.

EXAMPLE 1

Preparation of Multivesicular Liposome Formulations.

The first step in the preparation of multivesicular liposomes was the formation of a 'water-in-oil' emulsion. The first emulsion was prepared from a test lipid component containing 4 or 5 mL of a solution made of 13.20 mM of a test phosphatidylcholine (PC) with a chain length ranging from 12 to 22 carbons (either saturated or unsaturated) (Avanti Polar Lipids Inc., Alabaster, Ala.), 19.88 mM cholesterol (Spectrum Chemical Manufacturing Corporation, Gardena, Calif.), 2.79 mM 1,2-dipalmitoyl-sn-glycero-3-phosphoglycerol (DPPG), and 2.44 mM triolein (Avanti Polar Lipids) in chloroform. The lipid component was mixed with 4 or 5 mL of an aqueous drug solution to form a first aqueous solution containing one of the following drugs: cytarabine, leuprolide or morphine.

In the first mixing step, the mixture was emulsified using a TK model K Autohomogenizer at a speed of 9,000 rpm for 8 min. To the resulting first emulsion was added 20 mL of a solution containing 4 wt % glucose (Sigma Chemical Co., St. Louis, Mo.) and 40 mM lysine (Degussa Corp., Marceau, France). In the second mixing step, the mixture was emulsified again at a speed of 4,000 rpm for 60 sec using the model K Autohomogenizer. The resulting second emulsion, a 'water-in-oil-in-water' double emulsion, was transferred to a 1 L Erlenmeyer flask containing 30 mL of a solution of 4 weight % glucose and 40 mM lysine, with gentle swirling. Chloroform was evaporated by passing nitrogen gas over the emulsion at 37° C. for 20 min with gentle shaking. The resulting multivesicular liposomes were washed twice with 50 mL normal saline (0.9% sodium chloride) (McGaw Inc., Irvine, Calif.), or acidified saline, if needed to remove morphine crystals in some morphine formulations. The washed liposomes were centrifuged at 600×g on a bench top centrifuge, and the supernatant was decanted to yield a "final suspension" of 2–8 mL. In cases in which the main phase transition temperature of the test PC was close to or higher than the room temperature, an elevated temperature in the first mixing and second mixing step was usually used to make the multivesicular liposomes.

EXAMPLE 2

Determination of Encapsulation of Compound, Lipocrit, Percent Free Drug and Particle Size Distribution.

Each of the above-described preparations was characterized as follows:

Supernatant was obtained by centrifuging 0.2 mL of suspension for 3 min at 600×g in an Eppendorf centrifuge tube. For cytarabine and morphine formulations, 50 µL of the supernatant was withdrawn and pipetted into a glass tube containing 2 mL of 3:1 v/v isopropyl alcohol:1N hydrochloric acid (Fisher Chemical, Fair Lawn, N.J.), followed by rigorous mixing to obtain a clear solution. The absorbance at 280 nm for cytarabine or at 285 nm for morphine was measured on a U-2000 spectrophotometer (Hitachi Instruments Inc., Danbury, Conn.). For leuprolide formulations, 50 µL of the supernatant was withdrawn and pipetted into a glass tube containing 2 mL of 1:1 isopropyl alcohol:water titrated to pH 10 using 0.1 N ammonium hydroxide, followed by rigorous mixing to obtain a clear solution. The absorbance at 280 nm was then measured on the spectrophotometer. Similar absorbance assays were carried out for the liposome suspension except that a greater dilution was needed if the suspension contained a higher concentration of drug. A reference absorbance standard was established for each drug based on solutions of the test drug of known concentration in the test dissolving solution. The concentrations of drug in the suspension and supernatant were calculated based upon the reference absorbance standard using known methods.

Percent encapsulation of compound is the ratio of the amount of drug encapsulated to the amount of compound introduced prior to encapsulation times 100. Percent free drug is the ratio of the drug concentration exterior to the liposomes in the liposome suspension to the total amount of drug in the liposome suspension, multiplied by (100 minus the lipocrit).

Lipocrit was determined by the hematocrit method. About 50 µL of the multivesicular liposome suspension were taken up into a capillary tube. One end of the tube was sealed while ensuring that there were no air bubbles. Upon centrifugation at 600×g for 10 min, the suspension separated into a pellet layer and a supernatant layer. The percent ratio of the length of the tube occupied by the pellet to that occupied by the suspension was determined to calculate the lipocrit.

Particle size distribution and the mean diameter were determined by the method of laser light diffraction using an LA-500 or LA-910 Particle Size Analyzer (Horiba Inc., Irvine, Calif.).

When measurements were carried out in triplicate, the relative standard deviations were less than 3% for the encapsulation of compound and less than 10% for the total drug concentration, percent free drug, lipocrit, and mean particle diameter, as shown by the data in Table 1 below.

TABLE 1

Determination of the reproducibility of Cytarabine encapsulation in multivesicular liposomes of varied chain length and saturation

| Sample Preparation | [Cytarabine][1] mg/mL | % Encapsulation of compound | % Free | Lipocrit (in %) | Mean Particle Diameter, µm |
|---|---|---|---|---|---|
| DC16:1 Sample 1 | 10.0 | 30.6 | 4.6 | 30.7 | 9.9 |
| DC16:1 Sample 2 | 10.6 | 29.6 | 5.5 | 30.4 | 10.0 |
| DC16:1 Sample 3 | 9.8 | 30.1 | 5.4 | 29.7 | 10.1 |
| Mean ± SD | 10.1 ± 0.4 | 30.1 ± 0.5 | 5.2 ± 0.5 | 30.3 ± 0.5 | 10.0 ± 0.1 |
| RSD, % of mean | 4.0% | 1.7% | 9.6% | 1.6% | 1.0% |
| DC18:1 Sample 1 | 9.4 | 45.3 | 2.5 | 29.1 | 9.9 |
| DC18:1 Sample 2 | 9.7 | 44.7 | 2.9 | 29.5 | 9.9 |
| DC18:1 Sample 3 | 9.8 | 43.7 | 2.7 | 30.2 | 9.8 |
| Mean ± SD | 9.6 ± 0.2 | 44.6 ± 0.8 | 2.7 ± 0.2 | 29.6 ± 0.6 | 9.9 ± 0.1 |
| RSD, % of Mean | 2.1% | 1.8% | 7.4% | 2.0% | 1.0% |
| DC20:1 Sample 1 | 10.0 | 57.8 | 3.0 | 28.8 | 11.0 |
| DC20:1 Sample 2 | 10.2 | 55.7 | 2.9 | 29.8 | 10.9 |
| DC20:1 Sample 3 | 9.6 | 58.8 | 3.4 | 28.4 | 11.1 |
| Mean ± SD | 9.9 ± 0.3 | 57.4 ± 1.6 | 3.1 ± 0.3 | 29.0 ± 0.7 | 11.0 ± 0.1 |
| RSD, % of Mean | 3.0% | 2.8% | 9.7% | 2.4% | 0.9% |

[1][Cytarabine] stands for the concentration of cytarabine in the final liposome suspension.

EXAMPLE 3

The Dependence of Percent Encapsulation of Compound Upon PC Chain Length for Cytarabine in Multivesicular Liposomes.

Cytarabine was encapsulated into multivesicular liposomes as described above, but with 20 mg/ml cytarabine in 136 mM hydrochloric acid as the first aqueous solution. Five mL of the first aqueous solution was mixed with 5 mL of the test lipid combination solution to produce the first emulsion. Seven test lipid combination solutions containing different phospholipids with chain lengths from 12 to 20 carbons in length were prepared, each containing one of the following phospholipids: DC12:0PC, DC14:0PC, DC16:0PC, DC18:0PC, DC16:1PC, DC18:1PC, or DC20:1PC (Avanti Polar Lipids, Inc. Alabaster, Ala.). For the saturated phospholipids, DC14:0PC, DC16:0PC, DC18:0PC, the emulsification was carried out at about 45, 55 and 60° C., respectively. For the unsaturated phospholipids, DC16:1PC, DC18:1PC, and DC20:1PC, the emulsification was carried out at the ambient temperature (~23° C.). The percent encapsulation of compound for each formulation was determined, and the results are summarized in Table 2 below.

TABLE 2

Effect of phospholipid chain length on encapsulation efficiency of cytarabine in multivesicular liposomes

| Phospholipid | [Cytarabine][1] | % Encapsulation of compound | % Free | Lipocrit (in %) | Mean |
|---|---|---|---|---|---|
| Saturated PC | | | | | |
| DC12:0PC | 0.4 | 0.2 | — | — | — |
| DC14:0PC | 6.2 | 31.1 | 0.9 | 22.0 | 9.0 |
| DC16:0PC | 10.7 | 54.6 | 1.3 | 28.5 | 9.8 |
| DC18:0PC | 10.2 | 56.9 | 0.8 | 26.8 | 9.7 |
| Unsaturated PC | | | | | |
| DC16:1PC | 10.1 | 30.1 | 5.2 | 30.3 | 10.0 |
| DC18:1PC | 9.6 | 44.6 | 2.7 | 29.6 | 9.9 |
| DC20:1PC | 9.9 | 57.5 | 3.1 | 29.0 | 11.0 |

[1][Cytarabine] stands for the concentration of cytarabine in the final liposome suspension.

The data in Table 2 show that the encapsulation efficiency for cytarabine increases as the length of the carbon chain in the phospholipid increases, for both the saturated and unsaturated phospholipids. On the other hand, no obvious dependence of lipocrit or particle size upon lipid chain length is shown.

EXAMPLE 4
Freedom of Dependence of Percent Encapsulation of Compound Upon Other Lipids.

To determine whether the trend of increase in encapsulation of compound depends upon the chain length or number of carbons in a lipid other than the PC in the liposome formulation, DPPG in the cytarabine formulations of Example 3 was replaced with DOPG, which has a different carbon chain length and saturation. Three different lipid combination solutions were prepared, each one containing DOPG and one of the following phospholipids: DC16:1PC, DC18:1PC, or DC20:1PC. Since the phospholipids are unsaturated, the emulsification was carried out at the ambient temperature (≈23° C.). The results of these experiments are shown below in Table 3.

TABLE 3

Effect of varying the chain length of the phospholipid on encapsulation efficiency for cytarabine encapsulation into multivesicular liposomes

| Phospholipid | [Cytarabine][1] | % Encapsulation of compound | % Free | Lipocrit (in %) | Mean Particle |
|---|---|---|---|---|---|
| DOPG-DC16:1PC | 7.4 | 36.8 | 2.1 | 25.8 | 9.0 |
| DOPG-DC18:1PC | 9.6 | 47.3 | 1.7 | 30.5 | 10.0 |
| DOPG-DC20:1PC | 10.7 | 53.2 | 2.3 | 36.6 | 11.2 |

[1][Cytarabine] stands for the concentration of cytarabine in the final liposome suspension.

The results summarized in Table 3 show that even with the replacement of DPPG by DOPG, the trend of increasing encapsulation efficiency with increasing chain length in the liposome does not change. The relationship holds for both saturated and unsaturated phospholipids. A liposome formulated using DOPG and DC16:1PC, an unsaturated phospholipid with a single double bond and a 16 carbon chain, encapsulated cytarabine with 36.8% encapsulation efficiency; while the combination of DOPG and DC20:1PC, a phospholipid with a single double bond and a 20 carbon chain, encapsulated cytarabine with 53.2% encapsulation of compound.

EXAMPLE 5
Preparation of Multilamellar Liposomes (MLV) Encapsulating Cytarabine.

Multilamellar liposomes (MLV) were prepared by adding 20 mg/mL cytarabine (The Upjohn Co., Kalamazoo, Mich.) solution preheated to 60–65° C. into a test tube containing one of a series of test phosphatidylcholine (PC) having chain lengths ranging from 14 to 18 carbons (DCn:0PC, n=14–18) to make a 100 mM lipid dispersion. At 10 minute intervals for a total of five times, the dispersion was stirred in the test tube for 30 seconds using a vortexer (Baxter S/P Vortex Mixer) at the maximum speed. The dispersion was then allowed to undergo three cooling-heating cycles across the phase transition temperature of the test PC to facilitate drug equilibration across the bilayer membranes of the liposomes. The MLVs were then pelleted by centrifugation at 600×g and washed with normal saline (20:1 volume ratio). To ensure appropriate pellet washing, saline wash tests were conducted at various washing temperatures. It was found that a relatively thorough wash can be achieved with only two saline washes if the washing temperature is kept below the gel-liquid crystalline transition temperature of the test PC. For this reason, MLV made using DC14:0PC as the test PC were washed at 4° C., and those made using DC16:0PC or DC18:0PC as the test PC were washed at the ambient temperature. After the wash, the pellet was resuspended in normal saline.

EXAMPLE 6
Morphine

Morphine was encapsulated into multivesicular liposomes as described in Example 1 and characterized as described in Example 2 above, but with 36 mg/ml morphine sulfate pentahydrate (Mallinckrodt Chemical Inc., St. Louis, Mo.) in 100 mM hydrochloric acid as the first aqueous solution. Five mL of the first aqueous solution was mixed with 5 mL of the lipid combination solution to produce the first emulsion. For the saturated phospholipids, DC14:0PC, and DC18:0PC, the emulsification was carried out at two different temperatures, about 45 and 60° C., respectively. The results are summarized in Table 4.

TABLE 4

Effect of phospholipid chain length on encapsulation efficiency of morphine into multivesicular liposomes

| Phospholipid | [Morphine][1] (mg/mL) | % Encapsulation of compound | % Free | Lipocrit (in %) | Mean Particle Diameter (μm) |
|---|---|---|---|---|---|
| Saturated PC | | | | | |
| DC14:0PC | 13.9 | 38.7 | 1.7 | 27.6 | 9.2 |
| DC18:0PC | 20.1 | 55.6 | 0.7 | 32.9 | 9.5 |
| Unsaturated PC | | | | | |
| DC16:1PC | 12.8 | 35.5 | 7.7 | 20.2 | 9.8 |
| DC18:1PC | 21.5 | 59.8 | 1.3 | 36.5 | 9.5 |
| DC20:1PC | 24.6 | 68.3 | 0.9 | 37.6 | 9.6 |

[1][Morphine] stands for the concentration of morphine in the final liposome suspension As shown by the data in Table 4, the encapsulation of compound increases as the PC chain length increases for both saturated and unsaturated phospholipids.

EXAMPLE 7
Leuprolide

Leuprolide was encapsulated into multivesicular liposomes and characterized as described in Examples 1 and 2 above, but with the following modifications. Test lipid combination solutions of four mL made of 39.60 mM phosphatidylcholine (PC) of various chain length and saturation, 59.64 mM cholesterol, 9.37 mM DPPG, and 7.32 mM triolein in chloroform were each mixed with 4 mL of 10 mg/ml leuprolide acetate (Bachem Bioscience Inc., King of Prussia, Pa.) in 100 mM phosphoric acid to produce the first emulsion. The results are summarized in Table 5.

TABLE 5

Effect of phospholipid chain length on efficiency of encapsulating leuprolide into multivesicular liposomes

| Phospholipid | [Leuprolide]¹ (mg/mL) | % Encapsulation of compound | % Free | Lipocrit (in. %) | Mean Particle Diameter (μm) |
|---|---|---|---|---|---|
| Saturated PC | | | | | |
| DC12:0PC | 2.0 | 9.8 | 5.9 | 35.8 | 10.9 |
| DC14:0PC | 2.0 | 12.3 | 3.1 | 35.8 | 13.2 |
| DC16:0PC | 1.6 | 20.1 | 10.9 | 35.7 | 15.9 |
| DC18:0PC | 2.4 | 46.7 | 3.5 | 37.4 | 15.5 |
| DC20:0PC | 2.6 | 50.7 | 2.9 | 40.1 | 15.1 |
| Unsaturated PC | | | | | |
| DC18:1PC | 4.1 | 55.4 | 2.2 | 39.3 | 9.7 |
| DC22:1PC | 3.4 | 83.3 | 1.1 | 56.1 | 14.3 |

¹[Leuprolide] stands for the concentration of leuprolide in the final liposome suspension.

As shown by the data in Table 5, the drug encapsulation efficiency increases as the PC chain length increases for both saturated and unsaturated phospholipids.

EXAMPLE 8

Dependence on Chain Length of Encapsulation of Cytarabine Into Multilamellar Liposomes.

In order to determine whether the relationship between percent encapsulation of compound and lipid chain length applies to liposomes other than multivesicular liposomes, cytarabine was encapsulated into three different multilamellar liposomes, each prepared using a phospholipid with saturated carbon chains of 14, 16 or 18 carbons: DC14:0PC, DC16:0PC or DC18:0PC. The results are summarized in Table 6 below. From these results it is seen that, as is the case with multivesicular liposomes, the drug encapsulation efficiency of the multilamellar liposomes increases with the length of the carbon chain in the lipid.

TABLE 6

Effect of chain length on efficiency of encapsulating cytarabine in multilamellar liposomes

| Phospholipid | [Cytarabine]¹ (mg/mL) | % Encapsulation of compound | % Free | Lipocrit (in %) | Mean Particle Diameter (μm) |
|---|---|---|---|---|---|
| DC14:0PC | 1.03 | 6.5 | 1.2 | 14.0 | 4.7 |
| DC16:0PC | 1.85 | 11.6 | 1.1 | 16.7 | 4.1 |
| DC18:0PC | 3.54 | 44.2 | 0.4 | 24.6 | 4.7 |

¹[Cytarabine] stands for the concentration of cytarabine in the final liposome suspension

EXAMPLE 9

Dependence of Shelf-life on Chain Length and Chain Saturation for Multivesicular Liposomes Containing Cytarabine.

Figure 2:
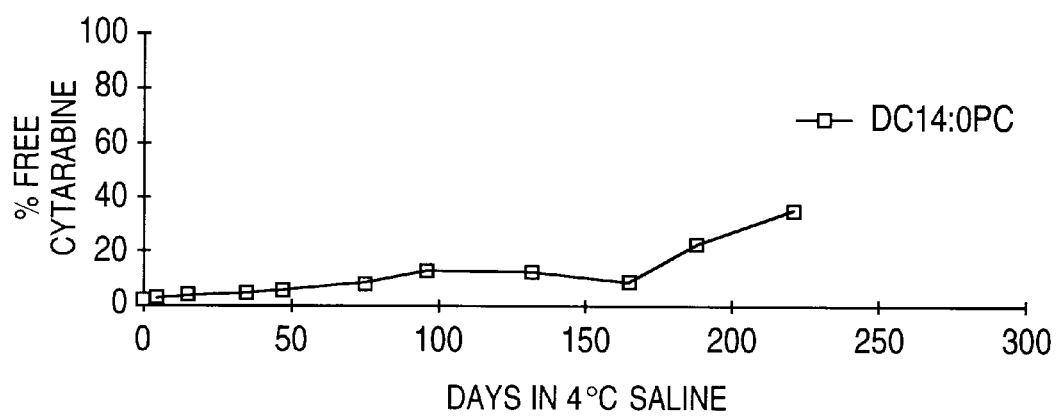
FIG. 2 is a graph illustrating the drug release profile at 4° C. of multivesicular liposomes made with DC14:0PC. The encapsulated drug is cytarabine.
Figure 3:
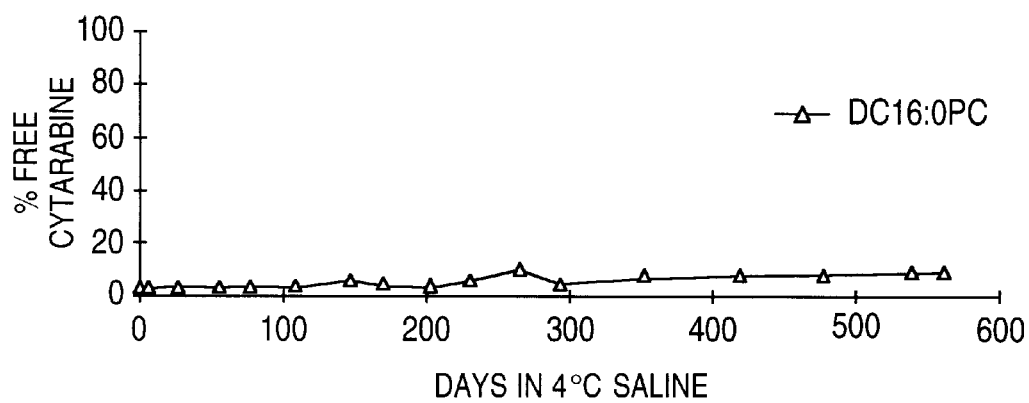
FIG. 3 is a graph illustrating the drug release profile at 4° C. of multivesicular liposomes made with DC16:0PC. The encapsulated drug is cytarabine.

To investigate the effects of lipid chain length on the shelf-life of multivesicular liposome formulations, a series of real time stability studies were conducted on formulations of multivesicular liposomes containing cytarabine and DC14:0PC, DC16:0PC and DC18:1PC. The formulations were made as described in Example 1 and characterized as described in Example 2. The results of the above stability studies are summarized in FIGS. 1–3. In this experiment, the shelf life stability of the formulations containing saturated PC with a carbon chain length of 14 or 16 carbons was greater than that of the formulation containing an unsaturated PC with a chain length of 18 carbons.

The foregoing description of the invention is exemplary for purposes of illustration and explanation. It should be understood that various modifications can be made without departing from the spirit and scope of the invention. Accordingly, the following claims are intended to be interpreted to embrace all such modifications.

We claims:

1. A method for increasing the percent of at least one compound encapsulated in a liposome made from a given formulation comprising:
   (a) forming a multivesicular liposome, by any conventional means, containing at least one encapsulated compound and having at least one first amphipathic lipid having a carbon chain from about 1 to about 12 carbons in the lipid component of the formulation;
   (b) determining the percent amount of encapsulated compound;
   (c) substituting said at least one first amphipathic lipid having a carbon chain from about 1 to about 12 carbons in the lipid component of the formulation with at least one second amphipathic lipid with a substantially similar chemical structure, having from 1 to 16 more carbons in a fatty acyl chain of the second lipid; wherein the increased number of carbons in the fatty acyl chain of the second lipid results in an increase in the percent of said at least one compound encapsulated in the formulation.

2. The method of claim 1 wherein the percent of the compound encapsulated is increased to a value between about 7.5 and 50 percent.

3. The method of claim 1 wherein the number of carbons is increased from 12 or less to a number in the range from 13 to about 22.

4. The method of claim 3 wherein the amphipathic lipid is a phospholipid.

5. The method of claim 3 wherein the amphipathic lipid is a saturated phospholipid.

6. The method of claim 3 wherein the percent of the compound encapsulated is increased to a value between about 30 and 85 percent.

7. The method of claim 4 wherein the phospholipid is selected from the group consisting of 1,2-dioleoyl-sn-glycero 3-phosphocholine,
   1,2-dilauroyl-sn-glycero-3-phosphocholine,
   1,2-dimyristoy-sn-glycero-3-phosphocholine,
   1,2-dipalmitoyl-sn-glycero-3-phosphocholine,
   1,2-distearoyl-sn-glycero-3-phosphocholine,
   1,2-diarachidoyl-sn-glycero-phosphocholine,
   1,2-dibehenoyl-sn-glycero-3-phospbocholine,
   1,2-dipalmitoleoyl-sn-glycero-3-phosphocholine,
   1,2-dieicosenoyl-sn-glycero-3-phosphocholine,
   1,2-dierucoyl-sn-glycero-3-phosphocholine,
   1,2-dipalmitoyl-sn-glycero-3-phosphoglycerol and
   1,2-dioleoyl-sn-glycero-3-phosphoglycerol,
   1,2-dioleoyl-sn-glycero-3-phosphoglycerol.

8. The method of claim 1 wherein the fatty acyl chain in the first amphipathic lipid contains 14 carbons and the increase is by a minimum of 2 carbons.

9. The method of clam 1 wherein the fatty acyl chain in the first lipid contains 16 carbons and the increase is by a mininimum of 2 carbons.

10. The method of claim 1 wherein the fatty acyl chain in the first lipid contains 18 carbons and the increase is by 2 carbons.

11. The method of claim 1 or 4 wherein the increase is by 4 carbons.

12. The method of claim 1 or 4 wherein the increase is by 6 carbons or more.

13. The method of claim 7 wherein the acyl chain is an $SN_1$ or an $SN_2$ chain, or both.

14. The method of claim 13 wherein the increase is in the $SN_1$ chain.

15. The method of claim 13 wherein the increase is in the $SN_2$ chain.

16. The method of claim 13 wherein the increase is in both the $SN_1$ chain and the $SN_2$ chain.

17. The method of claim 1 wherein steps (a) and (b) are performed only until the desired encapsulation efficiency is determined.

18. The method of claim 1 wherein only step (c) is performed once the desired formulation has been determined.

19. The method of claim 1 wherein 2 or more first amphipathic lipids having a carbon chain from about 1 to about 12 carbons in the lipid component of the formulation are substituted with second amphipathic lipids with substantially similar chemical structures, but having from 1 to 16 more carbons in the fatty acyl chains of the second lipid.

20. The method of claim 1 wherein 2 or more compounds are encapsulated.

* * * * *